United States Patent
Hodson et al.

(10) Patent No.: US 6,805,116 B2
(45) Date of Patent: Oct. 19, 2004

(54) INHALATION DEVICE

(75) Inventors: Darren Hodson, Shropshire (GB); Jørgen Rasmussen, Struer (DK)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/336,757

(22) Filed: Jan. 6, 2003

(65) Prior Publication Data

US 2003/0098024 A1 May 29, 2003

Related U.S. Application Data

(63) Continuation of application No. 09/822,252, filed on Apr. 2, 2001, now abandoned, which is a continuation of application No. 09/230,544, filed on Jan. 28, 1999, now abandoned.

(30) Foreign Application Priority Data

Nov. 14, 1997 (SE) .............................. 9704185
Nov. 11, 1998 (SE) ................... PCT/SE98/02040

(51) Int. Cl.$^7$ ............................................ A61M 11/00
(52) U.S. Cl. ......................... 128/200.23; 128/200.14; 128/202.27
(58) Field of Search ....................... 128/200.23, 203.23, 128/200.14, 203.12, 202.27, 200.22; 239/338

(56) References Cited

U.S. PATENT DOCUMENTS

| | | | |
|---|---|---|---|
| 3,739,950 A | 6/1973 | Gorman | |
| 3,841,533 A | 10/1974 | Carroll et al. | 128/200.23 |
| 4,291,688 A | 9/1981 | Kistler | 128/200.14 |
| 4,576,157 A | 3/1986 | Raghuprasad | 128/200.23 |
| 4,641,644 A | 2/1987 | Andersson et al. | |
| 5,447,151 A | 9/1995 | Bruna et al. | 128/203.15 |
| 5,460,171 A | 10/1995 | Pesenti et al. | 128/200.23 |
| 5,520,166 A | 5/1996 | Ritson et al. | |
| 5,564,414 A | 10/1996 | Walker et al. | 128/200.23 |
| 5,809,997 A | 9/1998 | Wolf | 128/200.23 |
| D416,998 S | 11/1999 | Hodson et al. | 128/200.23 |
| 6,044,841 A | 4/2000 | Verdun et al. | 128/200.14 |
| 6,293,279 B1 * | 9/2001 | Schmidt et al. | 128/200.23 |
| 6,345,617 B1 * | 2/2002 | Engelbreth et al. | 128/200.23 |

FOREIGN PATENT DOCUMENTS

| | | |
|---|---|---|
| WO | 95/07723 | 3/1995 |
| WO | 96/04948 | 2/1996 |

* cited by examiner

*Primary Examiner*—Henry Bennett
*Assistant Examiner*—Mital Patel
(74) *Attorney, Agent, or Firm*—Nixon & Vanderhye

(57) ABSTRACT

An actuator for an inhaler for administering medicament by inhalation, comprising: a main body (102) comprising an elongate tubular member (108) for receiving a canister (107) containing medicament and having a valve stem (111) extending therefrom, the tubular member (108) including a lateral opening (114) at one end thereof; and an outlet assembly (104) comprising a mouthpiece for guiding medicament to the mouth of a user and a nozzle block (120) for receiving the valve stem (111) of the canister (107) and delivering medicament from the canister (107) into the mouthpiece, the outlet assembly (104) being detachably mounted, through the lateral opening (114), to the main body (102) at an angle transverse to the length of the tubular member (108); characterized in that one of the main body (102) and the outlet assembly (104) further comprises at least one resiliently biased member, which is configured to engage with at least one part of the other of the main body (102) and the outlet assembly (104) and thereby hold the outlet assembly (104) to the main body (102), and at least one release component which in use is acted upon to enable release of the outlet assembly (104) from the main body (102).

24 Claims, 5 Drawing Sheets

INHALATION DEVICE

This application is a continuation of application Ser. No. 09/822,252, filed Apr. 2, 2001, now abandoned, which is a continuation of Ser. No. 09/230,544 filed Jan. 28, 1999 which is abandoned the entire content of which is hereby incorporated by reference in this application.

The present invention relates to an actuator for an inhaler for administering medicament by inhalation and to an inhaler including the same.

BACKGROUND OF THE INVENTION AND SUMMARY OF THE INVENTION

For some time, actuators have been known for delivering metered doses of medicament from aerosol canisters. These actuators comprise a single integral moulding and are usually coloured to identify the medicament being delivered. After use with only one canister the actuator is discarded. This is desirable, since some medicaments which are delivered, will, over time, become deposited in the nozzle block and the mouthpiece of the actuator.

It is an aim of the present invention to provide an actuator of two-part construction, with an outlet assembly thereof, which comprises those components which normally come into contact with medicament, being securely held in position in relation to the main body thereof even in the absence of an aerosol canister, but being capable of being detached as required.

The provision of a detachable outlet assembly is especially applicable where the actuator is sophisticated and hence relatively expensive, such as an actuator which includes a breath actuation mechanism or a compliance monitor, since it is not necessary to dispose of the entire actuator after exhaustion of the canister. Rather, a new outlet assembly may be fitted together with a new canister.

The two-part construction of an actuator further allows for the manufacture of a range of actuators by providing the outlet assembly as a first part common to the range and forming the main body as a second part from any material and optionally in any shape. Typically, the main body can be coloured or have a particular surface finish or decoration according to the medicament to be delivered. In addition, the main body can be formed to have a particular shape, such as that of an animal which may appeal to young children.

It will further be appreciated that this two-part construction is also advantageous for preparing regulatory documentation which will include common data relating to the outlet assembly.

WO-A-95/07723 discloses an actuator for an inhaler which includes a replaceable mouthpiece, but in the absence of an aerosol canister the mouthpiece can be slid out of the main body, thereby requiring no release component to effect release of the mouthpiece from the main body.

Accordingly, the present invention provides an actuator for an inhaler for administering medicament by inhalation, comprising: a main body comprising an elongate tubular member for receiving a canister containing medicament and having a valve stem extending therefrom, the tubular member including a lateral opening at one end thereof; and an outlet assembly comprising a mouthpiece for guiding medicament to the mouth of a user and a nozzle block for receiving the valve stem of the canister and delivering medicament from the canister into the mouthpiece, the outlet assembly being detachably mounted, through the lateral opening, to the main body at an angle transverse to the length of the tubular member; characterized in that one of the main body and the outlet assembly further comprises at least one resiliently biased member, which is configured to engage with at least one part of the other of the main body and the outlet assembly and thereby hold the outlet assembly to the main body, and at least one release component which in use is acted upon to enable release of the outlet assembly from the main body.

Preferably, the tubular member includes a further opening at the other end thereof through which a canister is in use fitted.

Preferably, the main body further comprises a foot at the one end of the tubular member which is configured such that, with a canister fitted therein, the actuator will stand unsupported with the tubular member extending generally vertically.

In one embodiment the bottom surface of the foot includes a recess for receiving a thumb or a finger of a user. Preferably, the recess is concave.

In another embodiment the bottom surface of the foot is flat.

Preferably, the actuator further comprises a breath actuation mechanism.

Preferably, the actuator further comprises a compliance monitor, in particular a dose counter.

In a preferred embodiment the main body comprises one or both of the breath actuation mechanism and the compliance monitor.

In a particularly preferred embodiment the foot comprises one or both of the breath actuation mechanism and the compliance monitor.

Preferably, the main body and the outlet assembly are composed of materials having different constitution.

In one embodiment the main body and the outlet assembly are composed of entirely different materials.

In another embodiment the main body and the outlet assembly are composed of the same basic material but include different additives such as colour pigment.

In a preferred embodiment the main body and the outlet assembly are of different colour.

Preferably, the outlet assembly is formed as a single integral moulding.

Preferably, the nozzle block includes a bore having an opening for receiving the valve stem of a canister and a spray orifice configured to direct a spray into the mouthpiece.

Preferably, the outlet assembly comprises first and second resiliently-biased arms which each support a catch member and the main body comprises first and second projections which extend inwardly from an inner surface thereof, the catch members on the first and second arms and the projections on the main body being arranged to engage one another when the outlet assembly is inserted fully into the main body.

Preferably, the first and second arms are radially opposed.

Preferably, the first and second arms extend rearwardly.

Preferably, the main body includes at least one opening for accessing the at least one release component.

More preferably, the at least one opening is provided in the foot of the main body.

Preferably, the at least one release component comprises a part which extends into or through the at least one opening.

More preferably, the at least one release component comprises first and second projections disposed on an interconnecting element which interconnects the catch members on the first and second arms such that when the projections on the interconnecting element are acted upon the catch members on the first and second arms are disengaged from the respective projections on the main body so as to allow withdrawal of the outlet assembly from the main body.

Preferably, the outlet assembly further comprises a further resiliently-biased arm which extends at an angle downwardly from the nozzle block, the distal end of the further arm including a catch member which, when the outlet assembly is inserted fully into the main body, engages behind a part of the tubular member defining the lateral opening.

More preferably, the further arm extends forwardly.

Preferably, the at least one release component further comprises a projection which extends downwardly from the further arm.

Preferably, the outlet assembly further comprises a second further resiliently-biased arm which supports a catch member, which, when the outlet assembly is inserted fully into the main body, engages behind a part of the tubular member defining the lateral opening.

More preferably, the second further arm extends rearwardly.

The present invention also extends to an inhaler comprising the above-described actuator and a canister containing medicament.

Preferably, the inhaler is a pressurised metered dose inhaler.

BRIEF DESCRIPTION OF THE DRAWINGS

A preferred embodiment of the present invention will now be described hereinbelow by way of example only with reference to the accompanying drawings, in which.

DETAILED DESCRIPTION OF PREFERRED EMBODIMENTS

Figure 1:
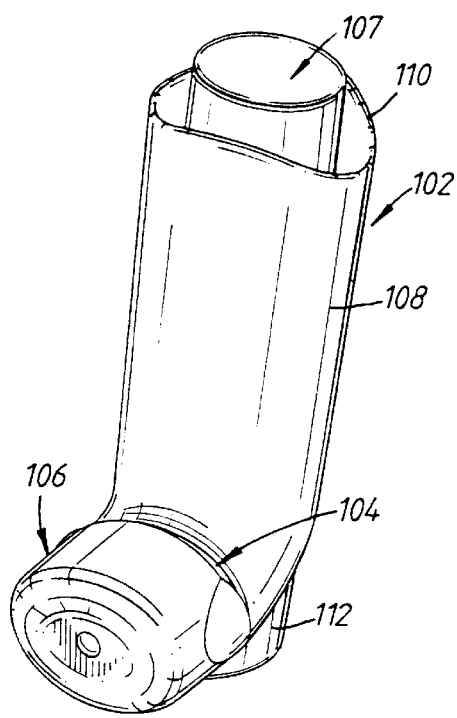
FIG. 1 illustrates a perspective view of an inhaler in accordance with a preferred embodiment of the present invention.
Figure 2:
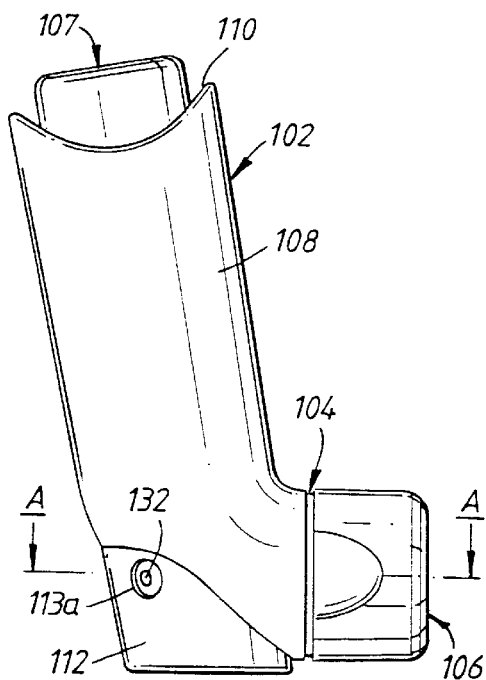
FIG. 2 illustrates a side view of the inhaler of FIG. 1.
Figure 3:
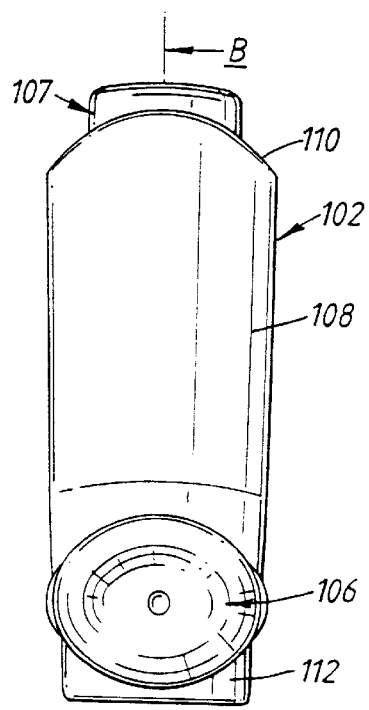
FIG. 3 illustrates a front view of the inhaler of FIG. 1.
Figure 4:
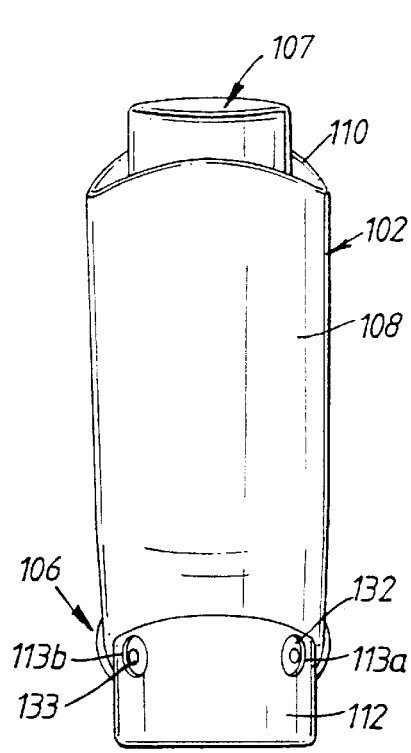
FIG. 4 illustrates a rear view of the inhaler of FIG. 1.
Figure 5:
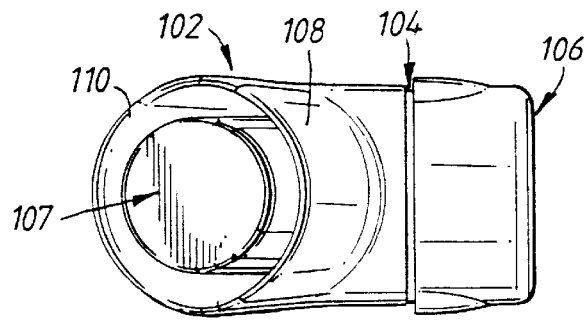
FIG. 5 illustrates a plan view of the inhaler of FIG. 1.
Figure 6:
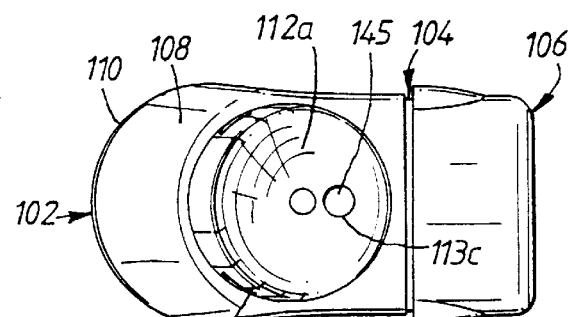
FIG. 6 illustrates an underneath plan view of the inhaler of FIG. 1.
Figure 7:
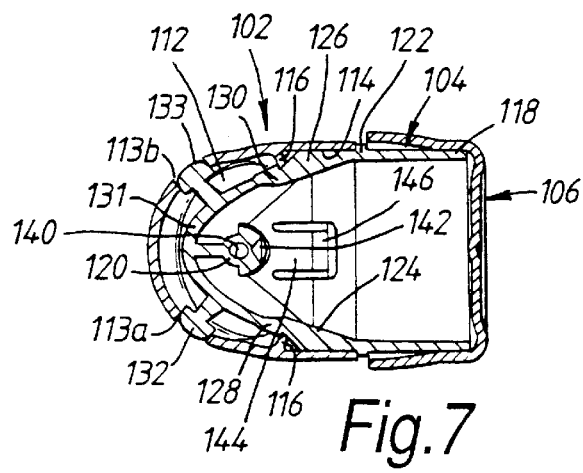
FIG. 7 illustrates a horizontal sectional view (along section A—A) of the inhaler of FIG. 1.
Figure 8:
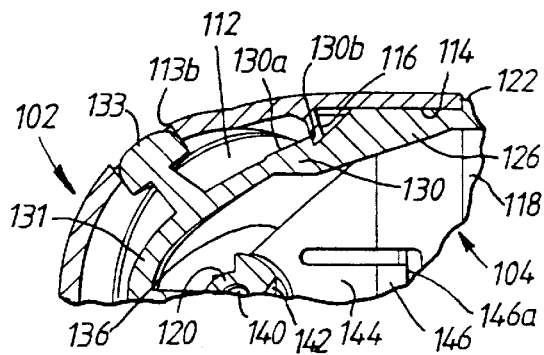
FIG. 8 illustrates in enlarged scale a fragmentary view of the section illustrated in FIG. 7.
Figure 9:
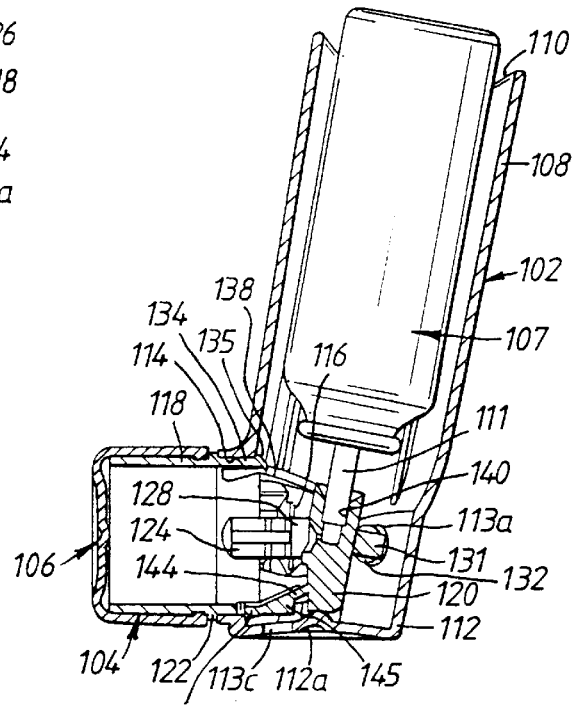
FIG. 9 illustrates a vertical sectional view (along section B—B) of the inhaler of FIG. 1.
Figure 10:
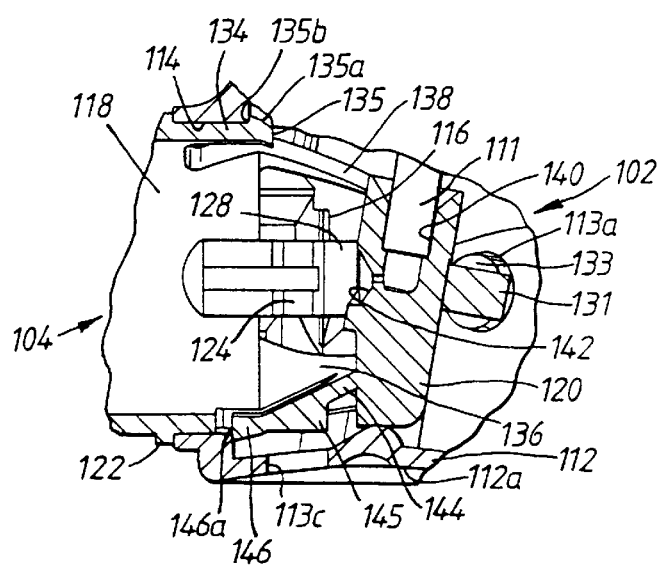
FIG. 10 illustrates in enlarged scale a fragmentary view of the section illustrated in FIG. 9.
Figure 11:
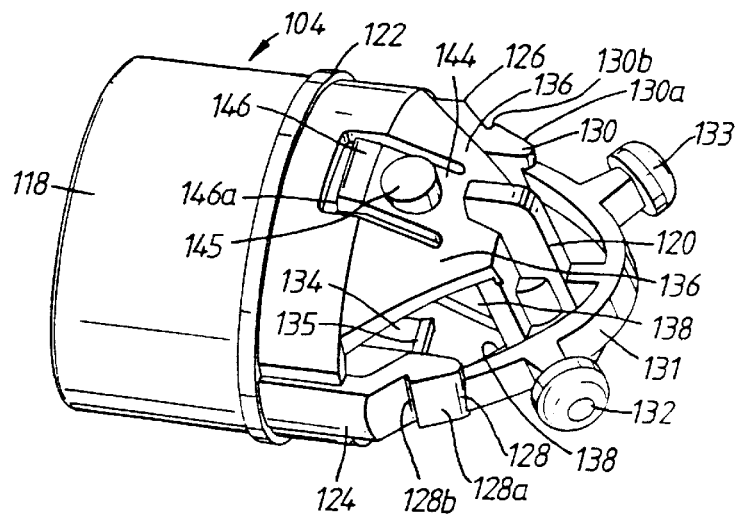
FIG. 11 illustrates a perspective view of the outlet assembly of the actuator of the inhaler of FIG. 1.
Figure 12:
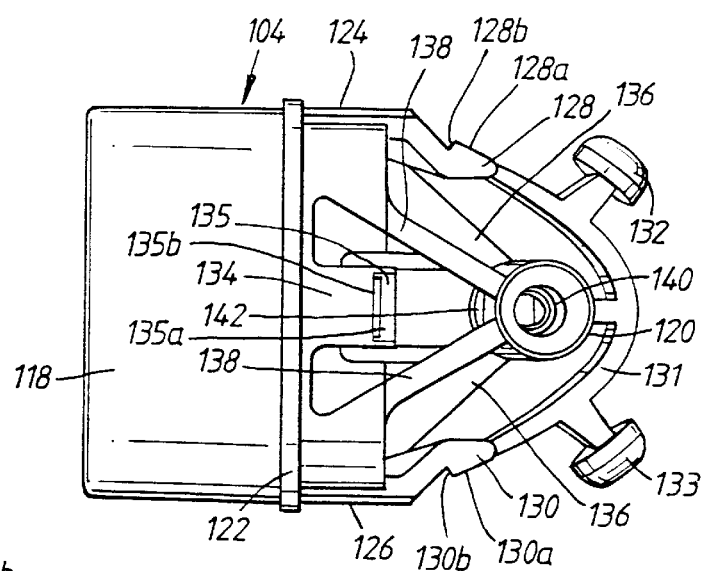
FIG. 12 illustrates a plan view of the outlet assembly of FIG. 11.
Figure 13:
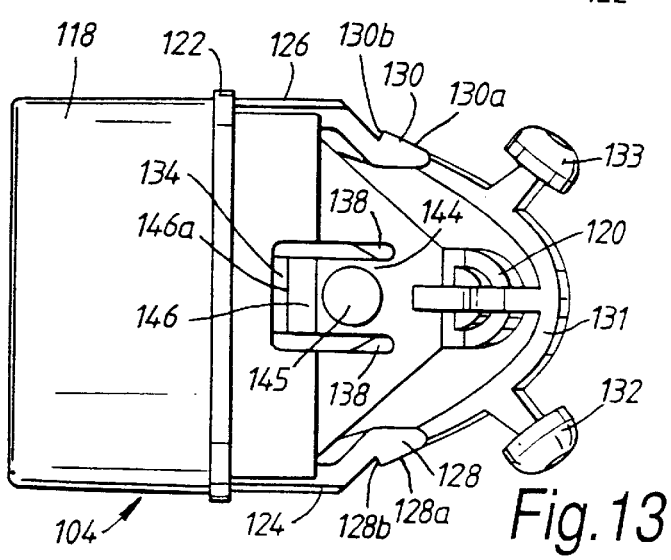
FIG. 13 illustrates an underneath plan view of the outlet assembly of FIG. 11.
Figure 14:
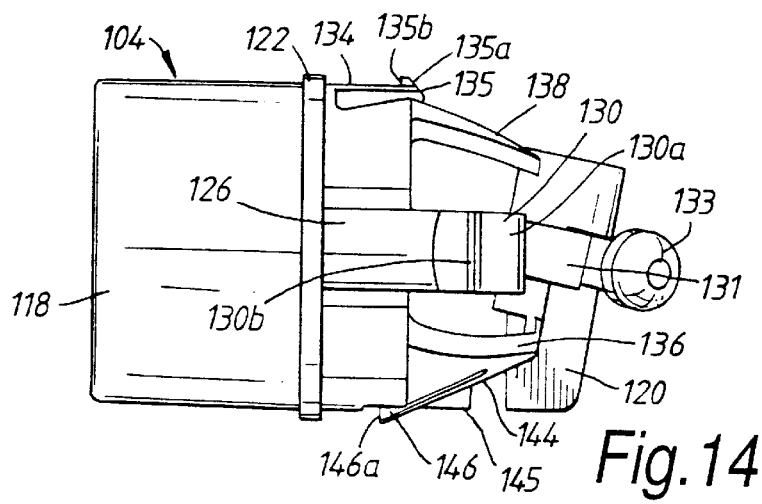
FIG. 14 illustrates a side view of the outlet assembly of FIG. 11.
Figure 15:
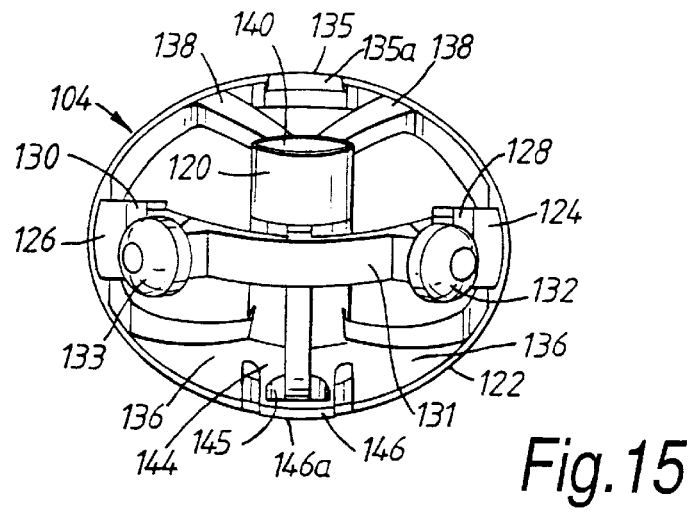
FIG. 15 illustrates a rear view of the outlet assembly of FIG. 11.
Figure 16:
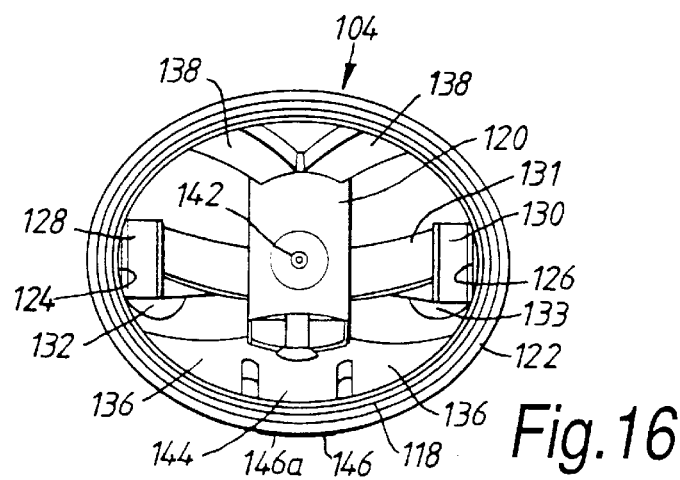
FIG. 16 illustrates a front view of the outlet assembly of FIG. 11.

The inhaler comprises an actuator, which comprises a main body 102, an outlet assembly 104 fitted to a lower part of the main body 102 and a cap 106, and an aerosol canister 107 containing medicament fitted therein.

The main body 102 comprises a tubular member 108 having an opening 110 at one, the upper, end thereof into which the canister 107 having a valve stem 111 extending therefrom is in use fitted, and a foot 112 having a bottom surface which includes a recess 112a, in this embodiment concave in shape, for receiving typically a thumb of a user. In an alternative embodiment the foot 112 can be formed with a substantially flat bottom surface. The foot 112 serves to allow the actuator to stand unsupported on a flat surface such that, when the actuator is not in use, it can be stored in an upright position. This is particularly advantageous when a canister 107 is fitted therein, since such canisters 107 should, ideally, be stored with the valve stem 111 directed downwards. The foot 112 includes first and second openings 113a, 113b in respective sides thereof and a third opening 113c in the bottom thereof. The other, lower, end of the tubular member 108 is closed and includes a lateral opening 114, in this embodiment ovoid in shape, into which the outlet assembly 104 is fitted.

The main body 102 further comprises a pair of opposing projections 116 which extend inwardly from the inner surface of the tubular member 108 adjacent the lateral opening 114. The projections 116 are disposed to the sides of the lateral opening 114 and are spaced rearwardly therefrom.

The outlet assembly 104 comprises a tubular section 118, a major part of which defines the mouthpiece which is in use gripped by the lips of a user, and a nozzle block 120 connected thereto.

The tubular section 118 includes a radial outwardly-directed peripheral flange 122. When the outlet assembly 104 is inserted fully into the main body 102, the flange 122 abuts the lateral opening 114 such that the major part of the tubular section 118 extends outwardly of the main body 102.

The outlet assembly 104 further comprises first and second arms 124, 126 which extend rearwardly form respective sides of the tubular section 118. Each of the first and second arms 124, 126 includes a catch member 128, 130 which is adapted to engage with a respective one of the projections 116 on the inner surface of the tubular member 108 when the outlet assembly 104 is inserted fully into the main body 102. The catch members 128, 130 on the first and second arms 124, 126 each include a first surface 128a, 130a which has a rearwardly-directed component and acts as a guiding surface, and a second surface 128b, 130b which is substantially orthogonally directed to the longitudinal axis of the outlet assembly 104 and acts as a locking surface.

The outlet assembly 104 also comprises an arcuate element 131 which interconnects the catch members 128, 130 on the first and second arms 124, 126 and is fixed at a mid-point to the nozzle block 120. The arcuate element 131 includes first and second outwardly-directed projections 132, 133 which, when the outlet assembly 104 is inserted fully into the main body 102, extend respectively into the first and second openings 113a, 113b in the main body 102 and act as release buttons as will be described hereinbelow.

The outlet assembly 104 further comprises a third arm 134 which extends rearwardly from the top of the tubular section 118. The third arm 134 includes a catch member 135 in the form of an outwardly-directed projection which, when the outlet assembly 104 is inserted fully into the main body 102, engages behind a part of the tubular member 108 defining the lateral opening 114. The catch member 135 on the third arm 134, as with the catch members 128, 130 on the first and second arms 124, 126, includes a first surface 135a which has a rearwardly-directed component and acts as a guiding surface, and a second surface 135b which is substantially orthogonally directed to the longitudinal axis of the outlet assembly 104 and acts as a locking surface.

The nozzle block 120 is connected to the tubular section 118 by first and second pairs of connecting elements 136, 138. The first pair of connecting elements 136 extend between a lower part of the nozzle block 120 and a lower part of the tubular section 118. The second pair of connecting elements 138 extend between an upper part of the nozzle block 120 and an upper part of the tubular section 118. The nozzle block 120 includes a tubular bore 140 which extends along the longitudinal axis of the tubular member 108 when the outlet assembly 104 is inserted fully into the main body 102. The tubular bore 140 is open at one, the upper, end and includes a laterally-directed spray orifice 142 at the other, lower, end. The spray orifice 142 is configured to direct a spray into the tubular section 118. In this embodiment the tubular bore 140 is adapted to receive the valve stem 111 of a canister 107.

The outlet assembly 104 further comprises a fourth arm 144 which extends forwardly and downwardly from the nozzle block 120. The distal end of the fourth arm 144 includes a catch member 146 which, when the outlet assembly 104 is inserted fully into the main body 102, engages behind a part of the tubular member 108 defining the lateral opening 114. The catch member 146 on the fourth arm 144 includes a surface 146a which is substantially orthogonally directed to the longitudinal axis of the outlet assembly 104 and acts as a locking surface. The fourth arm 144 further includes a downward projection 145 which, when the outlet assembly 104 is inserted fully into the main body 102, is located adjacent the third opening 113c in the main body 102 and acts as a release button as will be described hereinbelow.

In manufacture, an outlet assembly 104 and a main body 102 are selected according to the requirements, based on colour, shape, etc., for the inhaler. The outlet assembly 104 is then inserted into the lateral opening 114 in the main body 102 until the catch members 128, 130 on the first and second arms 124, 126 engage with the respective projections 116 on the inner surface of the tubular member 108 of the main body 102, and the catch members 135, 146 on the third and fourth arms 134, 144 engage behind respective parts of the tubular member 108 defining the lateral opening 114 in the main body 102. A canister 107 is then passed into the tubular member 108 of the main body 102 through the upper opening 110 such that the valve stem 111 of the canister 107 is located in the tubular bore 140 in the nozzle block 120. The inhaler is then ready for use.

By the provision of catch members the outlet assembly 104 is held securely in the main body 102 and a user is ordinarily prevented from removing the outlet assembly 104 from the main body 102. If the user wishes to re-use the main body 102 the exhausted canister 107 and then the outlet assembly 104 must be withdrawn. In order to withdraw the outlet assembly 104 the user first has to depress each of the projections 132, 133, 145 in the openings 113a, 113b, 113c in the foot 112 of the main body 102. In this embodiment, the projection 145 on the fourth arm 144 is depressed by passing an object into and through the opening 113c in the bottom of the foot 112. With the projections 132, 133, 145 depressed, the user then lifts up the outlet assembly 104 in relation to the main body 102 so that the catch member 135 on the third arm 134 clears the periphery of the lateral opening 114 and withdraws the outlet assembly 104 from the main body 102. The main body 102 can then be re-used by inserting a new outlet assembly 104 therein.

Finally, it will be understood by a person skilled in the art that the present invention is not limited to the described embodiment but can be modified in many different ways within the scope of the appended claims.

What is claimed is:

1. An actuator for an inhaler for administering medicament by inhalation, comprising:
    a main body comprising an elongate tubular member for receiving a canister containing medicament and having a valve stem extending therefrom, the tubular member including a lateral opening at one end thereof; and
    an outlet assembly comprising a mouthpiece for guiding medicament to the mouth of a user and a nozzle block for receiving the valve stem of the canister and delivering medicament from the canister when present into the mouthpiece, the outlet assembly being detachably mounted, through the lateral opening, to the main body at an angle transverse to the length of the tubular member;
    wherein one of the main body and the outlet assembly further comprises at least one resiliently biased member, which is configured to engage with at least one part of the other of the main body and the outlet assembly and thereby hold the outlet assembly to the main body, and at least one release component which in use is acted upon to enable release of the outlet assembly from the main body.

2. The actuator according to claim 1, wherein the tubular member includes a further opening at the other end thereof through which a canister is in use fitted.

3. The actuator according to claim 1, wherein the main body further comprises a foot at the one end of the tubular member which is configured such that, with a canister fitted therein, the actuator will stand unsupported with the tubular member extending generally vertically.

4. The actuator according to claim 3, wherein a bottom surface of the foot includes a recess for receiving a thumb or a finger of a user.

5. The actuator according to claim 4, wherein the recess is concave.

6. The actuator according to claim 3, wherein a bottom surface of the foot is flat.

7. The actuator according to any of claims 1, wherein the main body and the outlet assembly are composed of materials having different constitution.

8. The actuator according to claim 7, wherein the main body and the outlet assembly are of different colour.

9. The actuator according to claim 1, wherein the outlet assembly is formed as a single integral moulding.

10. The actuator according to claim 1, wherein the nozzle block includes a bore having an opening for receiving the valve stem of a canister and a spray orifice configured to direct a spray into the mouthpiece.

11. The actuator according to claim 1, wherein the outlet assembly comprises first and second resiliently-biased arms which each support a catch member and the main body comprises first and second projections which extend inwardly from an inner surface thereof, the catch members on the first and second arms and the projections on the main body being arranged to engage one another when the outlet assembly is inserted fully into the main body.

12. The actuator according to claim 11, wherein the first and second arms are radially opposed.

13. The actuator according to claim 11, wherein the first and second arms extend rearwardly.

14. The actuator according to claim 11, wherein the outlet assembly further comprises a further resiliently-biased arm which extends at an angle downwardly from the nozzle block, the distal end of the further arm including a catch member which, when the outlet assembly is inserted fully into the main body, engages behind a part of the tubular member defining the lateral opening.

15. The actuator according to claim 14, wherein the further arm extends forwardly.

16. The actuator according to claim 14, wherein the at least one release component further comprises a projection which extends downwardly from the further arm.

17. The actuator according to claim 11, wherein the outlet assembly further comprises a second further resiliently-biased arm which supports a catch member which, when the outlet assembly is inserted fully into the main body, engages behind a part of the tubular member defining the lateral opening.

18. The actuator according to claim 17, wherein the second further arm extends rearwardly.

19. The actuator according to any of claim 1, wherein the main body includes at least one opening for accessing the at least one release component.

20. The actuator according to claim 19, wherein the at least one opening is provided in the foot of the main body.

21. The actuator according to claim 19, wherein the at least one release component comprises a part which extends into or through the at least one opening.

22. The actuator according to claim 21, wherein the at least one release component comprises first and second projections disposed on an interconnecting element which interconnects the catch members on the first and second arms such that when the projections on the interconnecting element are acted upon the catch members on the first and second arms are disengaged from the respective projections on the main body so as to allow withdrawal of the outlet assembly from the main body.

23. An inhaler comprising the actuator according to claim 1 and a canister containing medicament.

24. The inhaler according to claim 23, wherein the inhaler is a pressurised metered dose inhaler.

* * * * *